United States Patent
Yamaguchi

(10) Patent No.: US 8,180,576 B2
(45) Date of Patent: May 15, 2012

(54) DATA PROCESSOR FOR MASS SPECTROMETER

(75) Inventor: Shinichi Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 628 days.

(21) Appl. No.: 12/300,373

(22) PCT Filed: May 11, 2006

(86) PCT No.: PCT/JP2006/309488

§ 371 (c)(1),
(2), (4) Date: Nov. 11, 2008

(87) PCT Pub. No.: WO2007/132502

PCT Pub. Date: Nov. 22, 2007

(65) Prior Publication Data

US 2009/0105964 A1    Apr. 23, 2009

(51) Int. Cl.
 *H01J 49/26* (2006.01)
 *G06F 17/00* (2006.01)
(52) U.S. Cl. ............... 702/22; 702/23; 702/27; 702/30; 702/32; 250/281; 250/282
(58) Field of Classification Search ............ 702/22, 702/23, 27, 30, 32
See application file for complete search history.

(56) References Cited

U.S. PATENT DOCUMENTS

| | | | |
|---|---|---|---|
| 6,907,352 B2 * | 6/2005 | Yoshinari et al. ............ | 702/23 |
| 2001/0052569 A1 * | 12/2001 | Bateman et al. ............ | 250/288 |
| 2004/0169138 A1 * | 9/2004 | Ootake et al. ............ | 250/281 |
| 2004/0181347 A1 * | 9/2004 | Yoshinari et al. ............ | 702/27 |
| 2005/0063864 A1 * | 3/2005 | Sano et al. ............ | 422/68.1 |

FOREIGN PATENT DOCUMENTS

| | | |
|---|---|---|
| EP | 1 376 651 A2 | 1/2004 |
| JP | 10-142196 A | 5/1998 |
| JP | 2001-249114 A | 9/2001 |
| JP | 2004-028782 A | 1/2004 |
| JP | 2004-257922 A | 9/2004 |
| JP | 2005-091344 A | 4/2005 |

OTHER PUBLICATIONS

Translation of JP 2004-028782, Jan. 29, 2004.*
Translation of JP 2004-257922, Sep. 16, 2004.*
Japanese Office Action corresponding to Japanese Patent Application No. 2008-515390, dated Sep. 14, 2010 (w/English translation).
Written Opinion of the International Searching Authority dated Aug. 15, 2006, issued in corresponding International application No. PCT/JP2006/309488.

* cited by examiner

*Primary Examiner* — Hal Wachsman
(74) *Attorney, Agent, or Firm* — Sughrue Mion, PLLC

(57) ABSTRACT

When a target substance's composition formula is deduced by using a mass spectrometer, if the target substance's composition formula is deduced based on an $MS^n$ spectrum and candidates are found, a composition formula candidate list including all the composition formula candidates is created, and the list is displayed in a list format. The composition formula candidates are narrowed down based on the $MS^n$ spectrum by an $MS^2$ analysis or $MS^3$ analysis. If there is a candidate to be excluded, the composition formula candidate list is updated, and the excluded candidate is moved to the exclusion list. Accompanying this, a composition formula candidate table is displayed in a list format on the display window. In this table, the composition formula candidates included in the exclusion list and the remaining composition formula candidates in the composition formula candidate list are simultaneously displayed with different colors so that they are visually discriminable.

9 Claims, 4 Drawing Sheets

Fig. 1
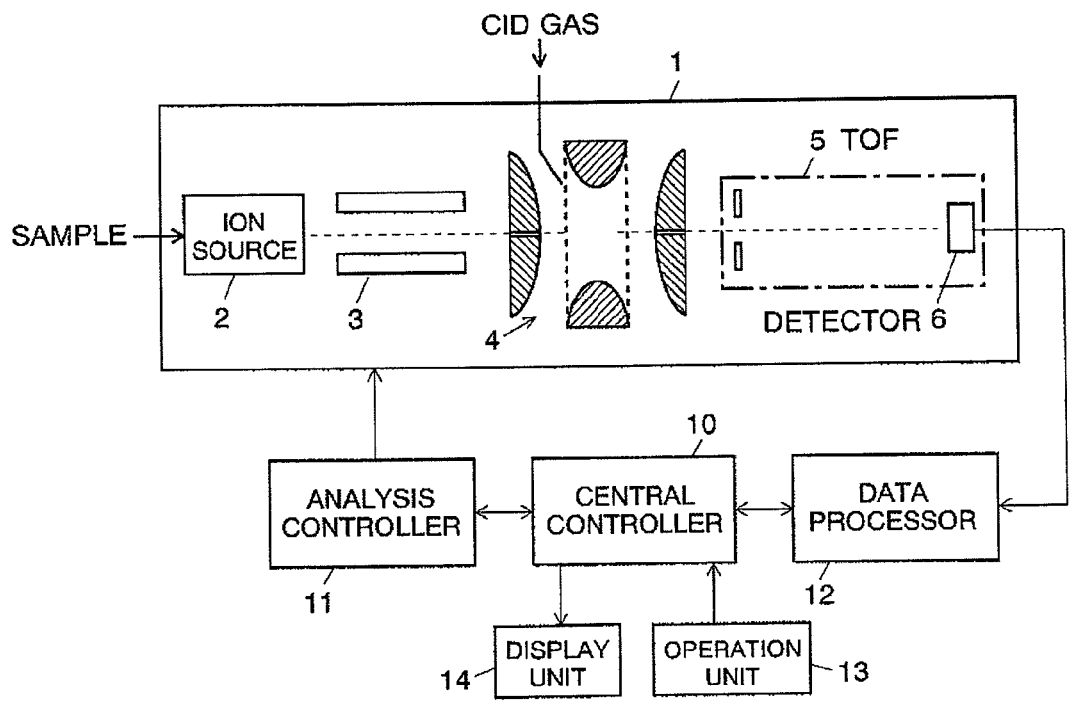
Fig. 2(a)     Fig. 3(b)
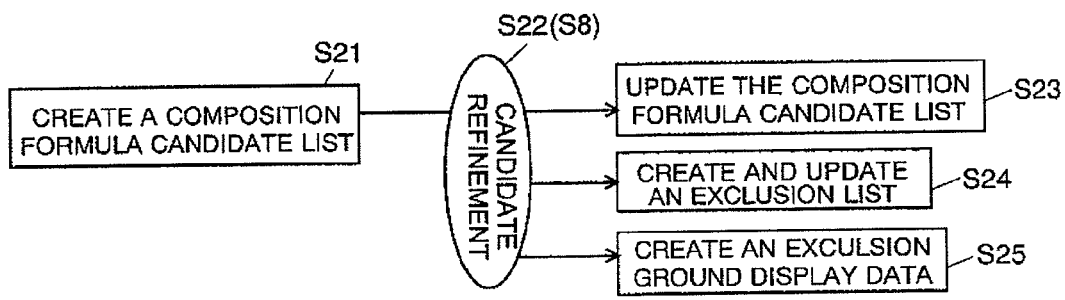

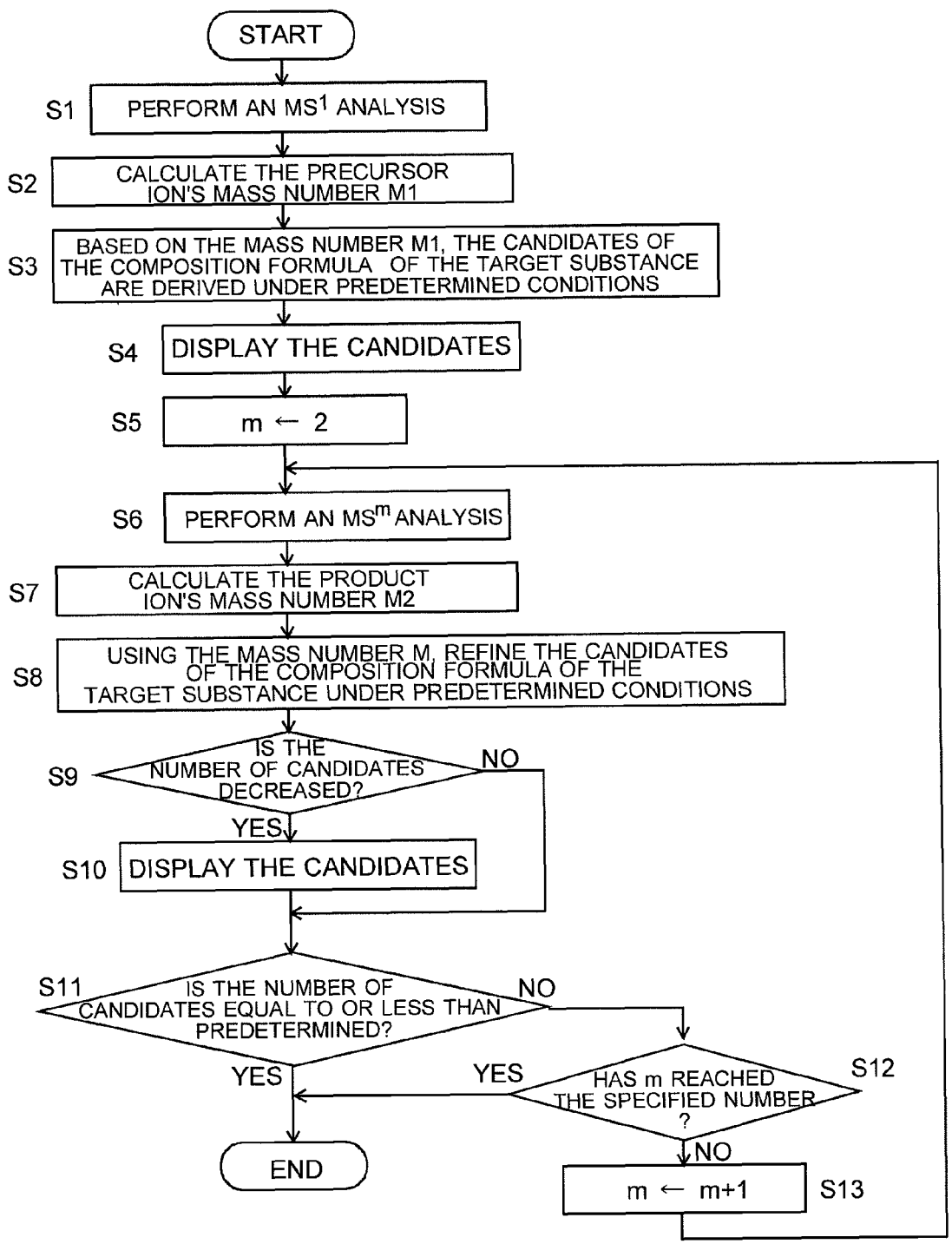
Fig. 4

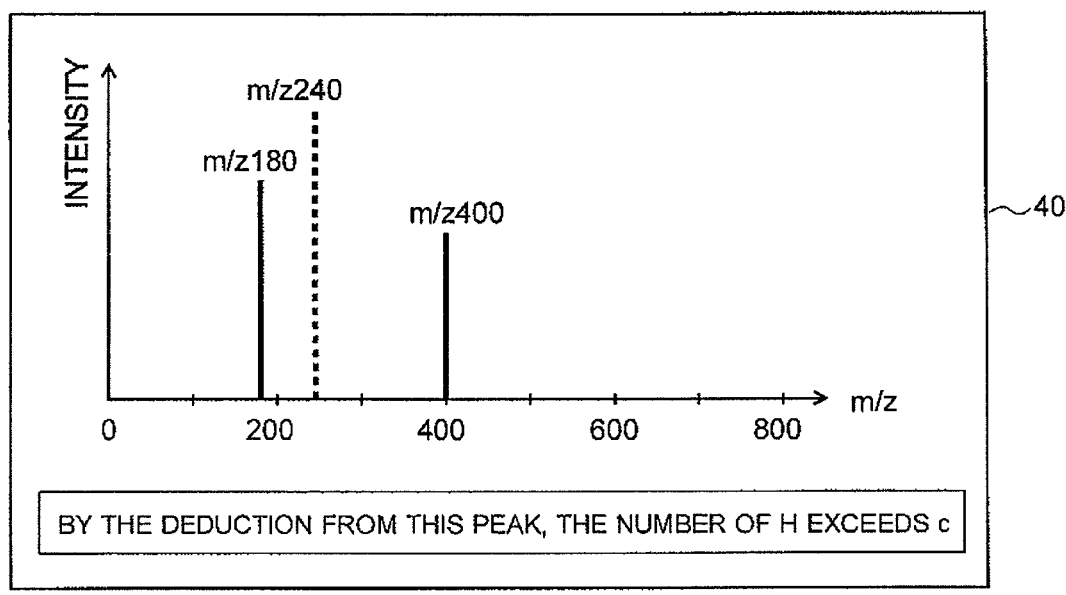

PRIOR ART
Fig. 8(a)
PRIOR ART
Fig. 8(b)
| 1 | CaHaOa |
|---|--------|
| 2 | CbHbOb |
| 3 | CcHcOc |
| 4 | CdHdOd |
| 5 | CeHeOe |
| 1 | CaHaOa |
|---|--------|
| 2 | CbHbOb |
| 3 | CdHdOd |
| 4 | CeHeOe |

DATA PROCESSOR FOR MASS SPECTROMETER

This application is a National Stage of International Application No. PCT/JP2006/309488 filed May 11, 2006.

TECHNICAL FIELD

The present invention relates to a data processor for a mass spectrometer, and more specifically to a data processor for processing the data obtained by a mass spectrometer which performs an $MS^n$ analysis.

BACKGROUND ART

One of well-known mass-analyzing methods using an ion trap mass spectrometer or other apparatuses is an MS/MS analysis (or tandem analysis). In a general MS/MS analysis, an ion having a specific mass number (mass-to-charge ratio m/z) is first selected as a precursor ion from an object to be analyzed. Next, the precursor ion thus selected is dissociated by a collision induced dissociation (CID) process to produce product ions. After that, the product ions are mass analyzed to obtain the information on the mass number of the product ions and desorbed ions, and based on the information, the composition and chemical structure of the target sample molecule are deduced.

In recent years, samples having larger molecular weight than before are becoming analyzed with such an apparatus, and their chemical structure (composition) also tends to become more complicated. Hence, depending on the quality of the sample, ions are often not dissociated to have a sufficiently small mass by only a one-stage dissociation operation. In such cases, an $MS^n$ analysis may be performed in which a dissociation operation is repeated more than once and the product ions finally generated are mass analyzed (refer to Japanese Unexamined Patent Application Publication No. H10-142196 and Japanese Unexamined Patent Application Publication No 2001-249114 for example). The aforementioned MS/MS analysis is an $MS^n$ analysis in the case where n=2.

In such an $MS^n$ analysis, the candidates for the molecular structure and composition of a target substance included in the original sample are basically narrowed down using both the composition formula by the combination of the elements deduced from the precursor ion's mass number and the combination of the elements deduced from the product ion's mass number. For a substance having a large molecular weight such as protein, in the case where the number of the dissociation process is relatively small such as $MS^2$ and $MS^3$, it is difficult to determine the composition formula since the number of the deduced composition formula's candidates is large. However, if the number of the dissociation process dissociation process is increased such as $MS^4$ and $MS^5$, the deduced composition formula's candidates become significantly narrowed down.

For example, in a prior art analysis, it is presumed that the composition formula of a target substance is deduced based on the result obtained by an MS analysis without a dissociation operation (i.e. an MS spectrum), and as a result, five composition formula candidates are lined up. These five composition formula candidates are displayed on a display window in a list format as illustrated in FIG. 8(a) for example. In practice, a, b, c, d, and e in FIG. 8 are each an appropriate number. Next, one precursor ion is selected using the MS spectrum to perform an MS2 analysis, and using the MS2 spectrum which is the analysis result, one ion is furthermore selected as a precursor ion to perform an MS3 analysis to obtain the MS3 spectrum. It is presumed that as the result of performing the refinement of the composition formulae using the information on the peaks appearing on the MS2 spectrum and MS3 spectrum, composition formula candidate number 3 in FIG. 8(a) is excluded and four composition formula candidates remain. This result is displayed on a display window in a list format as illustrated in FIG. 8(b) for example as in the case of FIG. 8(a).

Looking at the aforementioned displays, a person in charge of the analysis can visually and easily check the composition formula candidates remaining at the point in time of the $MS^3$ analysis. However, it is difficult to intuitively know which composition formula candidates are excluded from the result of the MS analysis in the refining process as described earlier. In the example of FIGS. 8(a) and 8(b), the constituent elements consist of only three kinds; carbon (C), hydrogen (H), and oxygen (O). If the kinds of the constituent elements are many, it is more difficult to know it.

The refining process for the composition formula candidates as previously described is automatically performed. Therefore, in some cases a person in charge of the analysis wants to confirm whether or not the refining process is precise and possesses high reliability. This is because, in the case where the refinement of the composition formula candidates is performed based on the information of the peak whose relative intensity is significantly low and its reliability is thought to be low, the reliability of the refining process itself can be thought to be low. However, with the conventional data processors, confirming which peak's information on the $MS^n$ spectrum is used as a base to exclude the composition formula candidates is not easy although possible: a complicated operation is required and the operability is not good.

DISCLOSURE OF THE INVENTION

Problem to be Solved by the Invention

The present invention is accomplished to solve the aforementioned problem, and the main objective thereof is to provide a data processor for a mass spectrometer allowing a person in charge of an analysis, when the chemical structure and composition formula of a target sample is deduced using an $MS^n$ spectrum obtained by an $MS^n$ analysis, to easily confirm and verify the appropriateness and content of the deduction process.

Means for Solving the Problems

The present invention accomplished to solve the aforementioned problem provides a data processor for a mass spectrometer, for processing data obtained by a mass spectrometer that performs an $MS^n$ analysis in which a process of selecting an ion having a specific mass-to-charge ratio from among ions produced by an $MS^{n-1}$ (where n is an integer equal to or more than 2) analysis, dissociating the ion, and performing a mass analysis of ions generated by a dissociation is repeated for n−1 stages, including:

a) a candidate refiner for deducing a composition formula of a target substance, based on data obtained by each $MS^m$ analysis while making m increase from 1 up to n so that candidates for the composition formula are narrowed down (or the number of candidates is decreased) in stages; and b) an information creator, which is a means for creating information to display a composition formula candidate deduced by the candidate refiner, for creating display information so that a composition formula candidate which has passed a refinement and a composition formula candidate excluded in a process of the refinement are displayed on the same display in a discriminable manner.

To be more precise for example, the information creator creates the display information so that the composition formula candidate which has passed the refinement and the excluded composition formula candidate are displayed with different display formats on the same list. The information creator creates the display information so that the composition formula candidate which has passed the refinement and the excluded composition formula candidate are displayed in each of the regions partitioned from each other in the same list. In addition, the information creator creates the display information so that the composition formula candidate which has passed a refinement and the excluded composition formula candidate are each displayed in a different list.

EFFECTS OF THE INVENTION

With the data processor for a mass spectrometer according to the present invention, as the candidates for the composition formula of a target substance are narrowed down in the process of performing an $MS^n$ analysis, not only are the remaining composition formula candidates displayed, but also the excluded composition formula candidates because it is judged to lack the consistency from the analysis result for example are simultaneously displayed on the display window. Therefore, even in the case where the composition formula is complicated, the person in charge of the analysis can visually, intuitionally, and immediately know the excluded composition formulae.

Preferably, the data processor for a mass spectrometer according to the present invention may further include a ground information collector for collecting ground information relating to grounds for the elimination of a composition formula candidate by the candidate refiner and storing it with information indicating the eliminated composition formula candidate, and a display based on the ground information can be performed on the display window responding to a predetermined indication.

A concrete example of the ground information in the present invention is a comment for explaining what kind of inconsistency has been found between the peak, which was the grounds for excluding a certain composition formula candidate, on the $MS^n$ spectrum and the composition formula candidates already lined up based on the peak.

With this configuration, in the case where a composition formula candidate is excluded in the course of the process of an $MS^n$ analysis, the person in charge of the analysis can promptly confirm whether or not the exclusion is appropriate, reliable, or the like. This allows a prompt and appropriate action, when a refining with little reliability is performed for example, such as: the analysis and process are immediately terminated or the analysis and process are redone changing the analysis conditions or the like. Hence, the operation such as the structural analysis of a target substance becomes more efficient and the analysis' accuracy is also enhanced.

BRIEF DESCRIPTION OF THE DRAWINGS

FIG. 1 is an overall configuration diagram of an embodiment of the mass analytical system including the data processor according to the present invention.

FIGS. 2(a) and 2(b) are diagrams illustrating an example of the display of the composition formula candidates in the mass analytical system according to the present embodiment.

FIG. 3 is a pattern diagram illustrating the outline of the display data processing when narrowing down the composition formula candidates in the mass analytical system according to the present embodiment.

FIG. 4 is a flowchart illustrating the analysis operation in the mass analytical system according to the present embodiment.

FIG. 5 is a diagram illustrating an example of the display content in the mass analytical system according to the present embodiment.

FIGS. 6(a) and 6(b) are diagrams illustrating another example of the display of the composition formula candidates in the mass analytical system according to the present embodiment.

FIGS. 7(a) and 7(b) are diagrams illustrating another example of the display of the composition formula candidates in the mass analytical system according to the present embodiment.

FIGS. 8(a) and 8(b) are diagrams illustrating an example of the display of the composition formula candidates in a prior art mass analytical system.

BEST MODE FOR CARRYING OUT THE INVENTION

One embodiment of the mass analytical system including the data processor according to the present invention will be described with reference to the figures. FIG. 1 is an overall configuration diagram of this mass analytical system.

A mass analyzer 1 includes: an ion source 2 for ionizing a sample molecule; an ion trap 4 for temporarily storing the ion in the internal space and for promoting the ion's CID in the internal space; an ion optical system 3 for introducing the ions generated in the ion source 2 to the ion trap 4; a time-of-flight mass separator (TOF) 5 for separating the ions released from the ion trap 4 according to the mass number; and a detector 6 for detecting the ions separated by the TOF 5.

An analysis controller 11 performs, based on the indication from the central controller 10, an $MS^n$ analysis by controlling the operation of each unit of the mass analyzer 1. A data processor 12 receives the detection data obtained by the detector 6 and performs a predetermined data processing including a display processing which will be described later. That is, the candidate refiner, the information creator, and the ground information collector in the present invention are functionally included in the data processor 12. To the central controller 10, an operation unit 13 and a display unit 14 are connected as a user interface. The central controller 10, analysis controller 11, and data processor 12 can be mostly realized by a personal computer including predetermined control/process software.

An example of a typical analysis operation executed, in the mass analytical system having the aforementioned configuration, under the overall control of the central controller 10 is roughly explained according to the flowchart of FIG. 4. The objective of this analysis operation is to obtain the composition formula of a target substance contained in the sample to perform the structural analysis of the target substance.

When an analysis is initiated responding to the indication by the person in charge of the analysis, a normal mass analysis without a dissociation operation inside the ion trap 4 ($MS^1$ analysis) is first performed (Step S1). That is, the target substance in the introduced sample is ionized in the ion source 2, the various kinds of ions generated are introduced to the ion trap 4 thorough the ion optical system 3, and in the ion trap 4, they are temporarily captured by the electric field formed by the voltage applied to the three-dimensional quadrupole electrodes. The ions captured are collectively launched at a predetermined timing to be introduced to the TOF 5. While flying in the flight space of the TOF 5, the time lag occurs for each ion according to the mass number and each ion reaches in sequence the detector 6 to be detected.

The data processor 12 which has received the detection data from the detector 6 converts the flight time in the TOF 5 into the mass number to create an MS spectrum, and finds the peak of the ion (i.e. precursor ion) originating from the target substance from among the peaks appearing on the MS spectrum to calculate its mass number M1 (Step S2).

Next, the data processor 12 refers to the database and computes, from the precursor ion's mass number M1, the composition formula candidates for the target substance in the sample under the predetermined analysis conditions (Step S3). In the present embodiment, the analysis conditions may include the kind and maximum number of each atom (or element) selected as a possible component in accordance with the kind of target substance and other factors, the mass accuracy of the mass analysis, and so on. That is, the number of each element is sequentially set under the given analysis conditions to combine each element, and the combination in which the mass conforms with that of the precursor ion is found. The number of composition formula candidates can be limited to some extent by the analysis conditions. However, if the analysis conditions are too severe, the actual composition formula might slip out from the candidates. Hence, the analysis conditions are required to be flexible to some extent. Given this factor, particularly in the case where the target substance's molecular weight is larger, the number of composition formula candidates to be obtained tends to be large. After obtaining the composition formula candidates as just described, the composition formula candidates' list is displayed on the display window of the display unit 14 via the central controller 10 (Step S4).

Next, the analysis repeat count parameter m is set to be 2 and $MS^m$ analysis is performed (Steps S5 and S6). That is, the target substance is ionized in the ion source 2, introduced to the inside of the ion trap 4, and the ions are temporarily captured by the electric field as described earlier. After that, the voltage which causes the undesired ions other than the precursor ion to disperse is applied to each electrode and only the precursor ion is left in the capture space; i.e. the precursor ion's selection is performed. Then, a CID gas is directed into the capture space from the outside so that the dissociation of the precursor ion is promoted by colliding with the CID gas.

The product ions generated by the dissociation are launched collectively at a predetermined timing, introduced to the TOF 5, separated according to the mass number by the TOF 5 in the similar manner as described earlier, and detected by the detector 6. In this manner, the mass number data of the product ion by an $MS^2$ analysis is obtained. Hence the data processor 12 creates an $MS^2$ spectrum based on this data, finds the peak of the product ion conforming with the analysis conditions among the peaks appearing on the $MS^2$ spectrum, and computes its mass number M2 (Step S7). Then, the data processor 12 refers to the database, and using the product ion's mass number M2, performs a refinement of the composition formula candidates obtained in Step S3 (Step S8). In particular, for example, the product ion's composition is deduced and the desorbed fragment's composition is also deduced. Then, in consideration of these deductions, in the case where there is a candidate lacking the consistency among the composition formula candidates, the candidate will be excluded.

As the result of the refinement, whether or not the number of composition formula candidates has decreased is determined (Step S9). In the case where it has decreased, a display which will be described later is performed on the display window of the display unit 14 via the central controller 10 so that the remaining composition formula candidates and the excluded composition formula candidates are discriminable (Step S10). If the number of composition formula candidates has not decreased in Step S9, Step S10 is passed over. Then, whether or not the number of the remaining composition formula candidates is equal to or less than a predetermined number (Step S11), and in the case where it is equal to or less than the predetermined number, it is determined that a sufficient refinement has been performed and the analysis and process are terminated.

On the other hand, in the case where it is determined that the number of composition formula candidates are not equal to or less than the predetermined number in Step S11, it is determined whether or not the analysis repeat count parameter m has reached a specified limit count (Step S12). In the case where it has not reached the limit, the analysis repeat count parameter m is incremented (Step S13) and the process returns to Step S6. The specified limit count determines the maximum number of the dissociation operation. After returning to Step S6, the number of the dissociation operation inside the ion trap 4 is increased. For example, if m=3, the ion selection and dissociation are performed two times, and the product ions generated as a result are mass analyzed in the TOF 5. Then, the subsequent process is performed in the same procedure as described earlier.

In the case where the target substance's molecular weight is large, while the number of the dissociating operation is small, it is difficult to narrow down the number of composition formula candidates based on the mass number of the product ions originating from the substance. However, as the dissociating operation's number increases, the product ion's mass itself becomes considerably small, which makes it easy to narrow down the composition formula candidates.

In the data processor 12 in the mass analytical system according to the present embodiment, in the process of deducing the target substance's composition formula by using the result of an $MS^n$ analysis as previously described, a characteristic operation is performed when creating the data for displaying the composition formula candidates and their pertinent information on the display unit 14. This operation is explained with reference to FIGS. 2, 3, and 5.

For example, when a plurality of composition formula candidates are lined up in Step S3, the data processor 12 creates a composition formula candidate list including all the composition formula candidates (Step S21). If the composition formula candidates lined up in this composition formula candidate list are displayed in a list form, it will be the composition formula candidate table 31 illustrated in FIG. 2(*a*). This is a conventional table.

If, as the result of a refinement for such composition formula candidates (Step S22) as described in Step S8, a composition formula candidate is excluded due to the lack of consistency, an update is performed so that the candidate is excluded from the composition formula candidate list (Step S23). At the same time, an exclusion list including this excluded composition formula candidate is created separately (Step S24). In the case where an exclusion list already exists, the update is performed so that the excluded composition formula candidate is added to the exclusion list. In addition, the exclusion ground display data is created for displaying the peak, which was the grounds for the exclusion in the case where a composition formula candidate is excluded from the composition formula candidate list, on the $MS^n$ spectrum and for displaying the comment information for showing the reason of the exclusion (Step S25).

When a composition formula candidate table is displayed on the display window of the display unit 14 in Step S10, the data processor 12 creates the display data so that the composition formula candidates which have already been moved to the exclusion list are displayed in the same display format of FIG. 2(*a*). However, their display color is set to be different from that of the candidates remaining in the composition formula candidate list. Hence, in the composition formula candidate table 32 displayed on the window of the display unit 14 as illustrated in FIG. 2(*b*), the content of the composition formulae is the same as FIG. 2(*a*), but the display colors of the candidates included in the composition formula candidate list and that of the candidates included in the exclusion list are different from each other. However, in FIG. 2(*b*), in place of using the display color difference, the candidate included in the exclusion list, i.e. the candidate number 3 (composition formula: CcHcOc), is illustrated with outline characters. In this manner, the display color in the displayed composition formula candidates changes with the progress of an $MS^n$ analysis. Therefore, the person in charge of the analysis can visually, intuitionally, and immediately grasp the excluded composition formulae.

When the person in charge of the analysis indicates, with the operation unit 13, the candidate number 3 whose display color is different from that of other candidates in the composition formula candidate table 32, the data processor 12 which has received the indication through the central controller 10 reads out the exclusion ground display data corresponding to the candidate, and then displays, by way of the central controller 10, the window 40 as illustrated in FIG. 5 on the display window of the display unit 14. The peak which has been the grounds for excluding the composition formula candidate is displayed with a different color so that it can be discriminated from the other peaks on the $MS^n$ spectrum in the window 40 (although it is illustrated with a dashed line in this figure). In addition, a comment for the reason of the exclusion based on the peak is displayed below the spectrum. Therefore, the person in charge of the analysis can easily know the grounds for the exclusion of the composition formula candidate and verify whether or not the grounds for the exclusion are reliable.

In the previous embodiment, the display color of the composition formula candidate excluded by the refinement process is set to be different from that of other candidates, i.e. the remaining composition formula candidates, so that it can be visually discriminated. However, in place of changing the color, it may be displayed with a different character style, or with a particular character decoration, e.g. a strike-through. Moreover, other display methods may be used as long as it can be easily visually discriminated. For example, as illustrated in FIG. 6(*b*), the remaining composition formula candidates and the excluded composition formula candidates may be respectively listed in the different tables 33 and 34. In addition, as illustrated in FIG. 7(*b*), the remaining composition formula candidates and the excluded composition formula candidates may be respectively listed in the clearly-partitioned regions in the same table 35.

It should be noted that the aforementioned examples are an example of the present invention, and it is evident that any modification, adjustment or addition properly made within the spirit of the preset invention is also covered within the scope of the present invention.

The invention claimed is:

1. A mass spectrometer that performs an $MS^n$ analysis in which a process of selecting an ion having a specific mass-to-charge ratio from among ions produced by an $MS^{n-1}$ (where n is an integer equal to or more than 2) analysis, dissociating the ion, and performing a mass analysis of ions generated by a dissociation is repeated for n−1 stages, the $MS^n$ analysis including a plurality of $MS^m$ analyses while making m increase from 1 up to n, comprising:
    a detector that detects data obtained by each $MS^m$ analysis so that candidates for a composition formula of a target substance is narrowed down in the n−1 stages; and
    a data processor, the data processor including
        a) a candidate refiner for deducing the composition formula of the target substance, based on the data obtained by each $MS^m$ analysis;
        b) an information creator, which is a means for creating information to display a composition formula candidate deduced by the candidate refiner, for creating display information so that a composition formula candidate which has passed a refinement and a composition formula candidate excluded in the refinement are displayed on a same display in a visually discriminable manner.

2. The mass spectrometer according to claim 1, wherein the information creator creates the display information so that the composition formula candidate which has passed a refinement and the excluded composition formula candidate are displayed with different display formats on a same list.

3. The mass spectrometer according to claim 2, the data processor further comprising a ground information collector for collecting ground information relating to grounds for an elimination of a composition formula candidate by the candidate refiner and storing the ground information with information indicating an eliminated composition formula candidate, wherein a display based on the ground information can be performed on a display window responding to a predetermined indication.

4. The mass spectrometer according to claim 1, wherein the information creator creates the display information so that the composition formula candidate which has passed a refinement and the excluded composition formula candidate are displayed in each of regions partitioned from each other in a same list.

5. The mass spectrometer according to claim 4, the data processor further comprising a ground information collector for collecting ground information relating to grounds for an elimination of a composition formula candidate by the candidate refiner and storing the ground information with information indicating an eliminated composition formula candidate, wherein a display based on the ground information can be performed on a display window responding to a predetermined indication.

6. The mass spectrometer according to claim 1, wherein the information creator creates the display information so that the composition formula candidate which has passed a refinement and the excluded composition formula candidate are each displayed in a different list.

7. The mass spectrometer according to claim 6, the data processor further comprising a ground information collector for collecting ground information relating to grounds for an elimination of a composition formula candidate by the candidate refiner and storing the ground information with information indicating an eliminated composition formula candidate, wherein a display based on the ground information can be performed on a display window responding to a predetermined indication.

8. The mass spectrometer according to claim 1, the data processor further comprising a ground information collector for collecting ground information relating to grounds for an elimination of a composition formula candidate by the candidate refiner and storing the ground information with information indicating an eliminated composition formula candidate, wherein a display based on the ground information can be performed on a display window responding to a predetermined indication.

9. The mass spectrometer according to claim 8, wherein the ground information is a comment for explaining what kind of inconsistency has been found between a peak, which has been the grounds for excluding a certain composition formula candidate, on an $MS^n$ spectrum and a composition formula candidate already lined up based on the peak.

* * * * *